United States Patent [19]

Neumann et al.

[11] Patent Number: 4,904,779

[45] Date of Patent: Feb. 27, 1990

[54] HETEROCYCLES BASED ON PIPERAZINOPIPERAZINE

[75] Inventors: Peter Neumann, Mannheim; Alexander Aumueller, Deidesheim; Hubert Trauth, Dudenhofen, all of Fed. Rep. of Germany

[73] Assignee: BASF Aktiengesellschaft, Ludwigshafen, Fed. Rep. of Germany

[21] Appl. No.: 299,423

[22] Filed: Jan. 23, 1989

[30] Foreign Application Priority Data

Jan. 23, 1988 [DE] Fed. Rep. of Germany ........ 3801944

[51] Int. Cl.$^4$ .............................. C07D 251/72
[52] U.S. Cl. .............................. 544/180; 524/89
[58] Field of Search .............................. 544/180

[56] References Cited

U.S. PATENT DOCUMENTS 4,835,273  5/1989  Aumueller .................. 544/180

FOREIGN PATENT DOCUMENTS 0213570  3/1987  European Pat. Off. .
0272589  6/1988  European Pat. Off. .
0272590  6/1988  European Pat. Off. .
2291203  6/1976  France .

Primary Examiner—Donald G. Daus
Attorney, Agent, or Firm—Oblon, Spivak, McClelland, Maier & Neustadt

[57] ABSTRACT

Heterocyclic compounds of the formula (I)

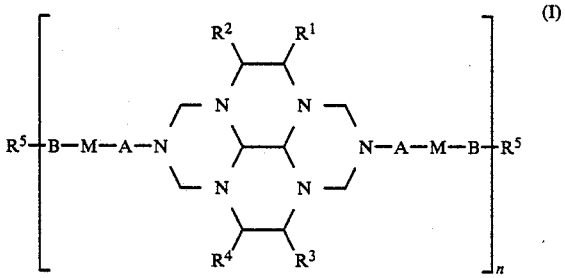

where
n is an integer from 1 to 70,
$R^1$, $R^2$, $R^3$ and $R^4$ are each independently of the others hydrogen, $C_1$-$C_{22}$-alkyl or $C_5$- or $C_6$-cycloalkyl or
$R^1$ and $R^2$ and also $R^3$ and $R^4$ are each pairwise trimethylene or tetramethylene,
A is a direct bond, $C_1$-$C_{22}$-alkylene, cycloalkylene,

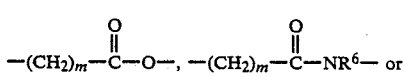

-continued $$-(CH_2)_m-\overset{O}{\underset{\|}{C}}-NH-(CH_2)_o-,$$

where
m and o are each from 1 to 20 and
$R^6$ is $C_1$-$C_{22}$-alkyl, $C_5$-$C_{12}$-cycloalkyl, $C_7$-$C_{18}$-phenylalkyl, unsubstituted or substituted phenyl or $C_2$-$C_{22}$-cyanoalkyl,
M is a group of the formula

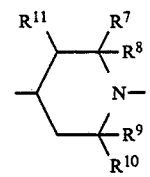

which may be bonded to A not only via the nitrogen but also via the carbon, and where
$R^7$, $R^8$, and $R^{10}$ are each independently of the others $C_1$-$C_4$-alkyl or
$R^7$ and $R^8$ and/or $R^9$ and $R^{10}$ are each pairwise tetramethylene or pentamethylene and
$R^{11}$ is hydrogen or $C_1$-$C_4$-alkyl,
B is a direct bond, $C_1$-$C_{22}$- alkylene, $C_7$-$C_{16}$-phenylalkylene or carbonyl-, carboxamido- or carboxylato-interrupted $C_3$-$C_{22}$-alkylene and
$R^5$ is hydrogen, cyano, hydroxyl,

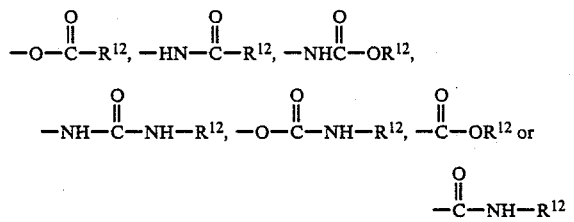

where
$R^{12}$ is hydrogen, $C_1$-$C_{22}$-alkyl, $C_5$-$C_{12}$-cycloalkyl, $C_7$-$C_{16}$-phenylalkyl, unsubstituted or substituted phenyl or 5- or 6- membered heterocyclyl or, when n is 1, M—B—$R^5$ is a group of the formula

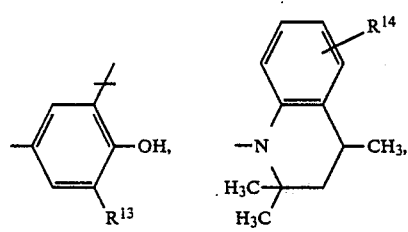

(Abstract continued on next page.)

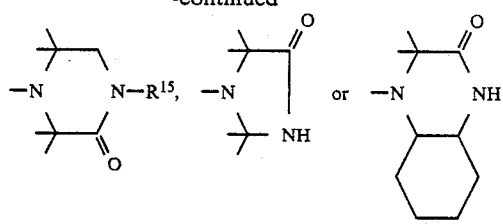
where
R$^{13}$ is C$_1$–C$_4$-alkyl,
R$^{14}$ is hydrogen, C$_1$–C$_4$-alkyl or C$_1$–C$_4$-alkoxy and
R$^{15}$ is C$_1$–C$_{12}$-alkyl, have very good stabilizing properties, no self-color, good compatibility with polymers, a low vapor pressure and stability to thermal decomposition.
14 Claims, No Drawings

HETEROCYCLES BASED ON PIPERAZINOPIPERAZINE

It is known that polyalkylpiperidine derivatives and sterically hindered phenols protect organic polymers from destruction by light and heat.

What is frequently unsatisfactory is the compatibility of these piperidine derivatives with polyolefins and other plastics, the duration of the protection, the self-color of the substances, and the tendency to volatility and the thermal decomposition of the stabilizers in the course of incorporation into polymers at elevated temperature.

It is an object of the present invention to provide novel stabilizers which avoid or do not have the foregoing disadvantages.

We have found that this object is achieved with the novel heterocycles of the present invention.

The present invention accordingly provides heterocycles of the general formula (I)

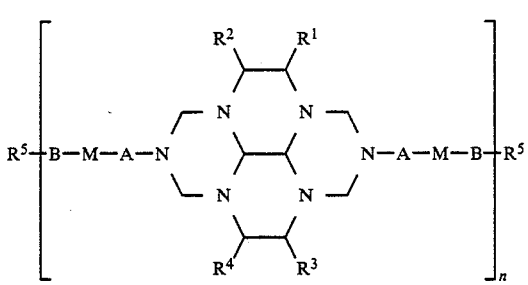

where n is an integer from 1 to 70, $R^1$, $R^2$, $R^3$ and $R^4$ are each independently of the others hydrogen, $C_1$–$C_{22}$-alkyl or $C_5$- or $C_6$-cycloalkyl or $R^1$ and $R^2$ and also $R^3$ and $R^4$ are each pairwise trimethylene or tetramethylene, A is a direct bond, $C_1$–$C_{22}$-alkylene, cycloalkylene,

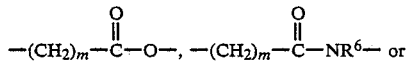

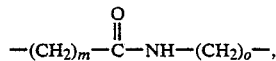

where m and o are each from 1 to 20 and $R^6$ is $C_1$–$C_{22}$-alkyl, $C_5$–$C_{12}$-cycloalkyl, $C_7$–$C_{18}$-phenylalkyl, phenyl or $C_2$–$C_{22}$-cyanoalkyl, M is a group of the formula

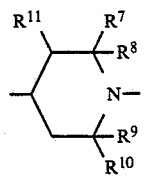

which may be bonded to A not only via the nitrogen but also via the carbon, and where $R^7$, $R^8$, $R^9$ and $R^{10}$ are each independently of the others $C_1$–$C_4$-alkyl or $R^7$ and $R^8$ and/or $R^9$ and $R^{10}$ are each pairwise tetramethylene or pentamethylene and $R^{11}$ is hydrogen or $C_1$–$C_4$-alkyl, B is a direct bond, $C_1$–$C_{22}$-alkylene, $C_7$–$C_{16}$-phenylalkylene or carbonyl-, carboxamido- or carboxylato- interrupted $C_3$–$C_{22}$-alkylene and $R^5$ is hydrogen, cyano, hydroxyl,

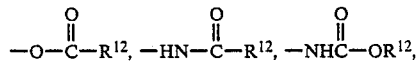

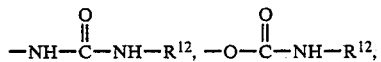

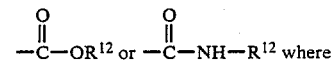

$R^{12}$ is hydrogen, $C_1$–$C_{22}$-alkyl, $C_5$–$C_{12}$-cycloalkyl, $C_7$–$C_{16}$-phenylalkyl, phenyl or 5- or 6-membered heterocyclyl or, when n is 1, M-B-$R^5$ is a group of the formula

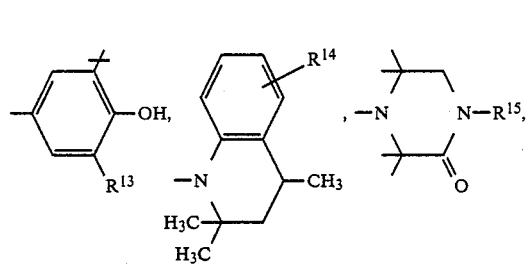

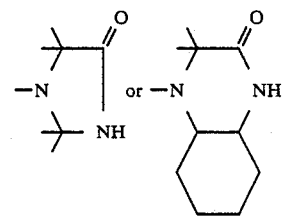

$R^{13}$ is $C_1$–$C_4$-alkyl, $R^{14}$ is hydrogen, $C_1$–$C_4$-alkyl or $C_1$–$C_4$-alkoxy and $R^{15}$ is $C_1$–$C_{12}$-alkyl.

The compounds according to the invention have extremely good stabilizing properties, no self-color, good compatibility with organic polymers and a low vapor pressure.

Preference is given to heterocycles (I) where $R^7$, $R^8$, $R^9$ and $R^{10}$ are each methyl and $R^{11}$ is hydrogen.

Preference is further given to compounds (I) where n is an integer from 1 to 10, in particular 1.

Alkyls $R^1$, $R^2$, $R^3$, $R^4$, $R^6$, $R^{12}$ and $R^{15}$ may be not only branched but also unbranched. Specific examples are: methyl, ethyl, propyl, i-propyl, butyl, isobutyl, pentyl, hexyl, octyl, decyl, lauryl, tetradecyl, hexadecyl and stearyl. $R^1$ to $R^4$ are each preferably methyl and in particular hydrogen.

Preference is also given to compounds of the formula (I) where not only $R^1$ and $R^2$ but also $R^3$ and $R^4$ are each pairwise tetramethylene.

Cycloalkyls $R^6$ and $R^{12}$ are for example cyclopentyl, cyclohexyl, cycloheptyl, cyclooctyl and cyclododecyl.

Phenylalkyls $R^6$ and $R^{12}$ are for example benzyl, methylbenzyl, 2- and 1-phenylethyl, 1-, 2- and 3-pentylpropyl and 1-, 2-, 3- and 4-phenylbutyl.

Phenyls $R^6$ and $R^{12}$ are specifically for example not only unsubstituted phenyl but also tolyl, methoxyphenyl, ethylphenyl, chlorophenyl, ethoxyphenyl and butoxyphenyl.

$C_1$–$C_4$-Alkoxy is for example methoxy, ethoxy, propoxy or butoxy.

Alkylenes A and B are for example —$(CH_2)_q$— where q is from 1 to 22.

Preferably, A and B are each a direct bond, methylene or ethylene.

Alkyl $R^{12}$ is preferably $C_1$–$C_4$-alkyl such as methyl, ethyl, propyl, isopropyl, butyl or isobutyl. $C_1$–$C_4$-alkyls $R^{13}$ and $R^{14}$ are for example: methyl, ethyl, propyl, i-propyl, butyl, i-butyl and tert-butyl. Preferred $R^{13}$ is methyl and in particular tert-butyl.

Heterocyclyl $R^{12}$ is derived for example from thiophene, furan or pyridine or a methyl derivative thereof.

The compounds of the general formula (I) may be prepared by reacting formaldehyde, paraformaldehyde or trioxane and piperazinopiperazines of the general formula (II) with compounds of the general formulae (III) and (IV), preferably in the presence of ion exchangers as catalysts.

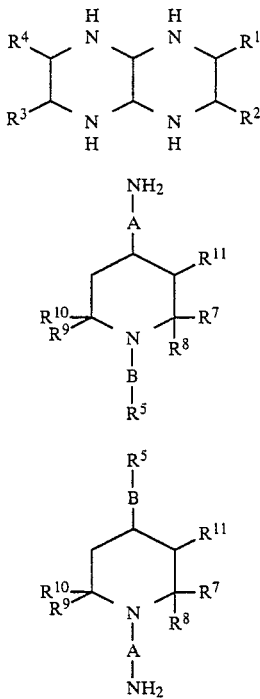

The solvent for this reaction is water or an organic solvent. Preference is given here to alcohols, in particular methanol and especially ethanol.

It is particularly advantageous to use cation exchangers, in particular sulfonato-containing insoluble polymers charged with alkali metal ions, for example sodium ions.

It is also possible to use mixtures of compounds of the general formulae (III) and (IV). Accordingly, the products are then mixtures of compounds of the general formula (II).

The starting materials of the general formula (II) are described for example in Rec. Trav. Chim. PaysBas 98, (1979), 326 and U.S. Pat. No. 2,345,237.

Compounds of the general formula (I) which still carry reactive groups can be converted by standard methods of organic chemistry, for example alkylation, acylation or cyanomethylation, into novel compounds of the general formula (II).

The compounds according to the invention may be present in the form of free bases or as salts. Suitable anions come for example from inorganic acids and in particular organic carboxylic acids and also organic sulfonic acids.

Inorganic anions are for example chloride, bromide, sulfate, methosulfate, tetrafluoroborate, phosphate and thiocyanate.

Carboxylic acid anions are for example formate, acetate, propionate, hexanoate, cyclohexanoate, lactate, stearate, dodecylbenzoate, benzoate, acrylate, methacrylate, citrate, malonate and succinate and also anions of polycarboxylic acids having up to 3,000 COOH groups.

Sulfonic acid anions are for example benzenesulfonate and tosylate.

The compounds according to the invention are suitable for stabilizing organic material, specifically plastics, against degradation by light and heat. They also act as metal deactivators. They are added to the plastics to be stabilized in a concentration of from 0.01 to 5% by weight, preferably from 0.02 to 2% by weight, before, during or after polymer formation.

To mix the compounds according to the invention with the plastics to be stabilized it is possible to use any existing apparatus and method for mixing stabilizers or other additives into polymers.

The plastics stabilized with one of the compounds according to the invention may additionally contain further additives, for example antioxidants, light stabilizers, metal deactivators, antistats, flame retarders, pigments and fillers.

Antioxidants and light stabilizers which may be added to the plastics besides the compounds according to the invention are for example compounds based on sterically hindered phenols or sulfur- or phosphorus-containing costabilizers.

Such phenolic antioxidants are for example 2,6-di-tert-butyl-4-methylphenol, n-octadecyl β-(3,5-di-tert-butyl-4-hydroxyphenyl)propionate, 1,1,3-tris(2-methyl-4-hydroxy-5-tert-butylphenyl)butane, 1,3,5-trimethyl-2,4,6-tris(3,5-di-tert-butyl-4-hydroxybenzyl)isocyanurate, 1,3,5-tris[β-(3,5-di-tert-butyl-4-hydroxyphenyl)-propionyloxyethyl]isocyanurate, 1,3,5-tris(2,6-dimethyl-3-hydroxy-4-tert-butylbenzyl)isocyanurate and pentaerythritol tetrakis[β-(3,5-di-tert-butyl-4-hydroxyphenyl)-propionate].

Phosphorus-containing antioxidants are for example tris(nonylphenyl)-phosphite, distearyl pentaerythritol diphosphite, tris(2,4-di-tert-butylphenyl)-phosphite, tris(2-tert-butyl-4-methylphenyl) phosphite, bis(2,4-di-tert-butylphenyl)-pentaerythritol diphosphite and tetrakis(2,4-di-tert-butylphenyl)-4,4'-biphenylene diphosphite.

Sulfur-containing antioxidants are for example dilauryl thiodipropionate, dimyristyl thiodipropionate, distearyl thiodipropionate, pentaerythritol tetrakis(β-laurylthiopropionate) and pentaerythritol tetrakis(β-hexylthiopropionate).

Further antioxidants and light stabilizers which may be used together with the compounds according to the invention are for example 2-(2'-hydroxyphenyl)benzotriazoles, 2-hydroxybenzophenones, aryl esters of hydroxybenzoic acids, α-cyanocinnamic acid derivative, nickel compounds and oxalic dianilides.

Organic polymers which can be stabilized with the compounds according to the invention are for example:

polymers of mono- and diolefins, for example polyethylene of low or high density, linear polyethylene of low density, polypropylene, polyisobutylene, polybutene-1, polyisoprene, polybutadiene and also copolymers of mono- or diolefins or mixtures thereof;

copolymers of mono- or diolefins with other vinylmonomers, for example ethylene/alkyl acrylate copolymers, ethylene/alkyl methacrylate copolymers, ethylene/vinyl acetate copolymers or ethylene/acrylic acid copolymers;

polystyrene;

copolymers of styrene or α-methylstyrene with dienes or acrylic derivatives, for example styrene-butadiene, styrene-acrylonitrile, styrene/ethyl methacrylate, styrene/butadiene/ethyl acrylate, styrene-acrylonitrile-methacrylate;

ABS, MBS or similar polymers;

halogen-containing polymers, for example polyvinyl chloride, polyvinyl fluoride, polyvinylidene fluoride and copolymers thereof;

polymers derived from $\alpha,\beta$-unsaturated acids and derivatives thereof, such as polyacrylates and polymethacrylates, polyacrylamides and polyacrylonitriles;

polymers derived from unsaturated alcohols and amines or acrylic derivatives or acetals thereof, such as polyvinyl alcohol or polyvinyl acetate;

polyurethanes, polyamides, polyureas, polyesters, polycarbonates, polysulfones, polyether sulfones and polyether ketones.

Further organic polymers which may be stabilized with the compounds according to the invention are industrial coatings. Of these, it is baking finish coatings, more particularly automotive coatings, preferably two-build coatings, which deserve a special mention.

Here too the abovementioned antioxidants and light stabilizers may be used in addition.

The compounds according to the invention may be added to the coating composition in solid or dissolved form. Here their excellent solubility in coating systems is a particular advantage.

It is preferred to use the compounds according to the invention for stabilizing polyolefins, preferably ethylene and propylene polymers, and also coatings and polyurethanes.

The invention is explained in more detail by the following examples:

EXAMPLE 1

56.8 g of 1,4,5,8-tetraazadecalin, 48 g of paraformaldehyde, 124.8 g of 2,2,6,6-tetramethyl-4-aminopiperidine and 20 g of Lewatit ® S100 were stirred at room temperature in 400 ml of ethanol for 6 hours. The precipitate was made to dissolve by heating, the solution was filtered while still hot, and the filtrate was cooled in an ice bath. Filtration with suction left compound (V) in the form of colorless crystals of melting point 233°-235° C. On recrystallization from hexane the melting point rose to 236°-238° C.

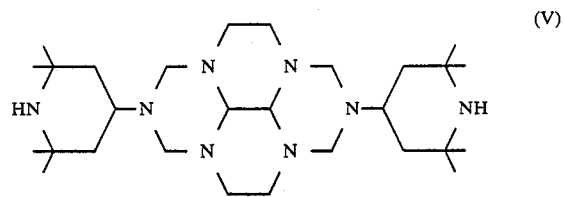

EXAMPLE 2

17 g of 2,6-dimethyl-1,4,5,8-tetraazadecalin, 12 g of paraformaldehyde, 31.2 g of 2,2,6,6-tetramethyl-4-aminopiperidine and 5 g of Lewatit ® S100 were stirred at room temperature in 100 ml of ethanol for 6 hours. The catalyst was removed by filtration, and the filtrate was evaporated down to almost dryness. The residue was twice decocted with hot water, dried and recrystallized from toluene, leaving compound (VI) in the form of colorless crystals of melting point 220°-224° C.

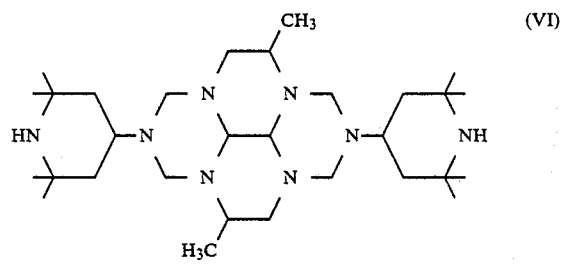

EXAMPLE 3

7.51 g of perhydro-5,6,11,12-tetraazatetracene, 3.6 g of paraformaldehyde, 9.36 g of 2,2,6,6-tetramethyl-4-aminopiperidine and 2 g of Lewatit ® S100 were boiled in 50 ml of ethanol for 5 hours. The catalyst was filtered off, the filtrate was evaporated down, the residue was boiled up in 150 ml of n-hexane, and the solution was filtered off with suction, giving compound (VII) in the form of slightly brownish crystals of melting point 232°-235° C.

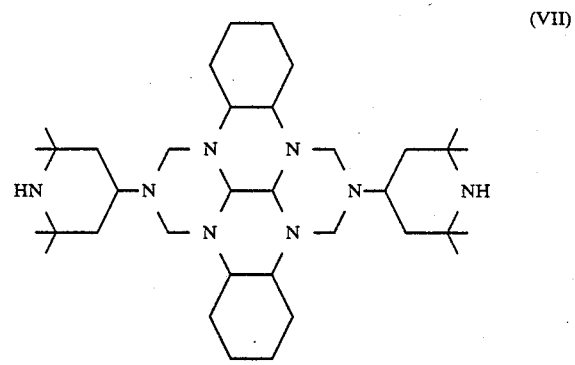

EXAMPLE 4

14.2 g of 1,4,5,8-tetraazadecalin, 12 g of paraformaldehyde, 40 g of 2,2,6,6-tetramethyl-1-[2-aminoethyl]-4-hydroxypiperidine and 5.1 g of Lewatit ® S100 were boiled in 250 ml of ethanol for 9.5 hours. The resulting precipitate was filtered off with suction, washed with ethanol and recrystallized from DMF, leaving compound (VIII) as a colorless solid of melting point 293°–294° C.

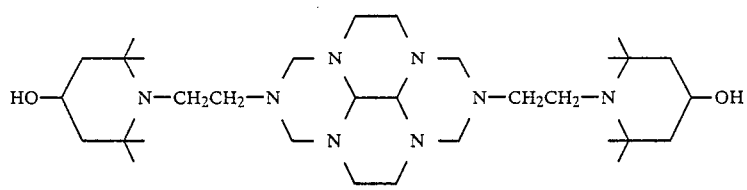

EXAMPLE 5

4.7 g of 1,4,5,8-tetraazadecalin, 4 g of paraformaldehyde, 15.7 g of 4-aminomethyl-2,6-di-t-butylphenol and 1.7 g of Lewatit ® S100 were boiled in 250 ml of ethanol for 4.5 hours. The resulting precipitate was filtered off with suction and recrystallized from i-butanol, giving compound (IX) as a colorless solid of melting point 249° C.

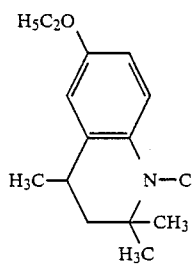 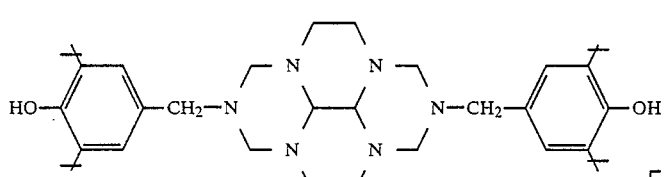

EXAMPLE 6

5 ml of ethanol saturated with potassium carbonate, 6 g of paraformaldehyde, 0.46 g of potassium carbonate and 17 g of acetonecyanohydrin were stirred at 25°–30° C. for 2 hours. The mixture was brought to pH 6 with phosphoric acid. Thereafter 25.1 g of the product of Example 1 and 50 ml of ethanol were added, and the mixture was refluxed for 4 hours. It was then filtered with suction, and the residue was decocted with water and dried, leaving compound (X) as a colorless solid of melting point 270°–273° C.

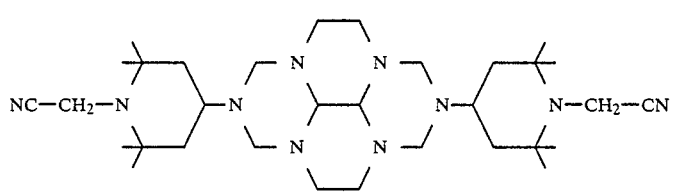

EXAMPLE 7

6.2 g of 1,4,5,8-tetraazadecalin, 29 g of 1-[2-aminoethyl]-6-ethoxy-1,2,3,4-tetrahydro-2,2,4-trimethyl-quinoline, 5.3 g of paraformaldehyde and 2.5 g of Lewatit ® S100 were refluxed in 200 ml of ethanol for 7 hours. The residue was filtered off with suction and recrystallized twice from n-butanol, giving compound (XI) as a colorless solid of melting point 184°–185° C.

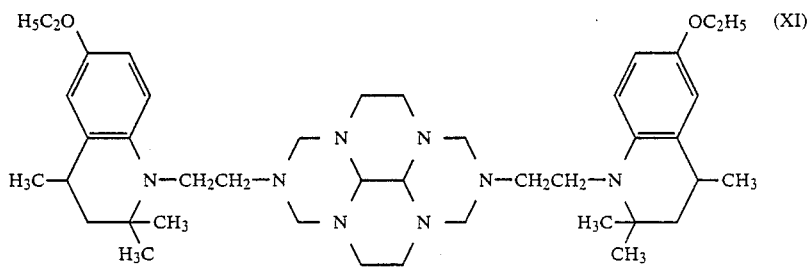

We claim:
1. A heterocyclic compound of the formula (I)

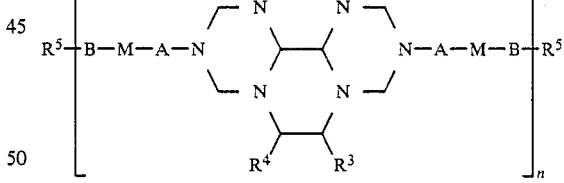

where
n is an integer from 1 to 70,
$R^1$, $R^2$, $R^3$ and $R^4$ are each independently of the others hydrogen, $C_1$–$C_{22}$-alkyl or $C_5$- or $C_6$-cycloalkyl or $R^1$ and $R^2$ and also $R^3$ and $R^4$ are each pairwise trimethylene or tetramethylene, A is a direct bond, $C_1$–$C_{22}$-alkylene, cycloalkylene,

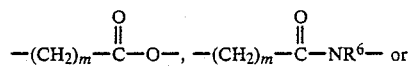

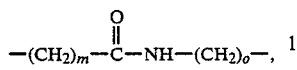

where
m and o are each from 1 to 20 and
$R^6$ is $C_1$–$C_{22}$-alkyl, $C_5$–$C_{12}$-cycloalkyl, $C_7$–$C_{18}$-phenyl-, alkyl, phenyl, $C_1$–$C_4$-alkyl-, $C_1$–$C_4$-alkoxy- or chlorine-substituted phenyl or $C_2$–$C_{22}$-cyanoalkyl,
M is a group of the formula

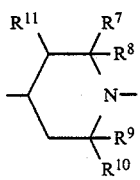

which may be bonded to A not only via the nitrogen but also via the carbon, and where
$R^7$, $R^8$, $R^9$ and $R^{10}$ are each independently of the others $C_1$–$C_4$-alkyl or
$R^7$ and $R^8$ or $R^9$ and $R^{10}$ or $R^7$ and $R^8$ and $R^9$ and $R^{10}$ are each pairwise tetramethylene or pentamethylene and
$R^{11}$ is hydrogen or $C_1$–$C_4$-alkyl,
B is a direct bond, $C_1$–$C_{22}$-alkylene, $C_7$–$C_{16}$-phenylalkylene or carbonyl-, carboxamido- or carboxylato- interrupted $C_3$–$C_{22}$-alkylene and
$R^5$ is hydrogen, cyano, hydroxyl,

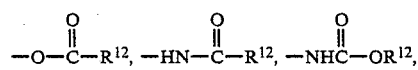

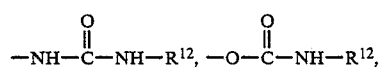

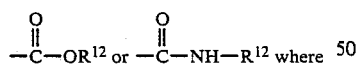

$R^{12}$ is hydrogen, $C_1$–$C_{22}$-alkyl, $C_5$–$C_{12}$-cycloalkyl, $C_7$–$C_{16}$-phenylalkyl, phenyl, $C_1$–$C_4$-alkyl-, $C_1$–$C_4$-alkoxy- or chlorine-substituted phenyl or 5- or 6-membered heterocyclyl or, when n is 1, M-B-$R^5$ i a group of the formula

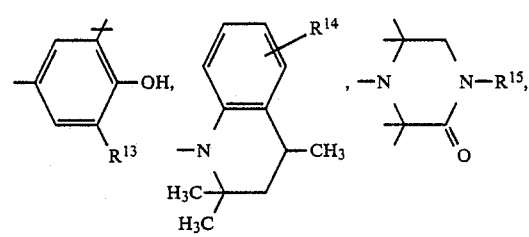

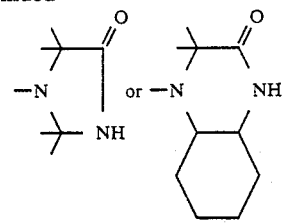

where
$R^{13}$ is $C_1$–$C_4$-alkyl,
$R^{14}$ is hydrogen, $C_1$–$C_4$-alkyl or $C_1$–$C_4$-alkoxy and
$R^{15}$ is $C_1$–$C_{12}$-alkyl.

2. A heterocyclic compound as claimed in claim 1, wherein $R^7$, $R^8$, $R^9$ and $R^{10}$ are each methyl.

3. A heterocyclic compound as claimed in claim 1, wherein $R^{11}$ is hydrogen.

4. A heterocyclic compound as claimed in claim 2, wherein $R^{11}$ is hydrogen.

5. A heterocyclic compound as claimed in claim 2, wherein n is from 1 to 10.

6. A heterocyclic compound as claimed in claim 4, wherein n is from 1 to 10.

7. A heterocyclic compound as claimed in claim 2, wherein n is 1.

8. A heterocyclic compound as claimed in claim 4, wherein n is 1.

9. A heterocyclic compound as claimed in claim 1, wherein A or B or A and B are each a chemical bond, —$CH_2$— or —$CH_2$—$CH_2$—.

10. A heterocyclic compound as claimed in claim 4, wherein A or B or A and B are each a chemical bond, —$CH_2$— or —$CH_2$—$CH_2$—.

11. A heterocyclic compound as claimed in claim 6, wherein A or B or A and B are each a chemical bond, —$CH_2$— or —$CH_2$—$CH_2$—.

12. A heterocyclic compound as claimed in claim 7, wherein A or B or A and B are each a chemical bond, —$CH_2$— or —$CH_2$—$CH_2$—.

13. A heterocyclic compound as claimed in claim 8, wherein A or B or A and B are each a chemical bond, —$CH_2$— or —$CH_2$—$CH_2$—.

14. A heterocyclic compound of the formula (I)

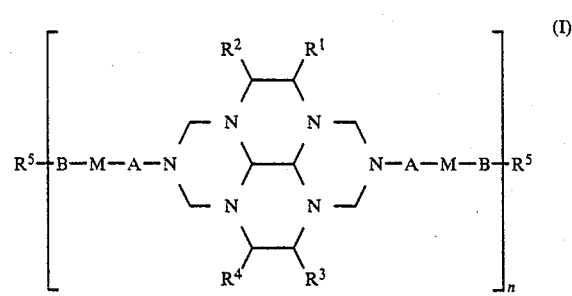

where
n is 1,
$R^1$, $R^2$, $R^3$ and $R^4$ are each independently of the others hydrogen or methyl or
$R^1$ and $R^2$ and also $R^3$ and $R^4$ are each pairwise trimethylene or tetramethylene,
A is a direct bond, —$CH_2$— or —$CH_2$—$CH_2$—,
M is a group of the formula

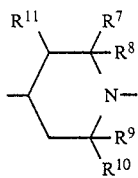
which may be bonded to A not only via the nitrogen but also via the carbon, and where
$R^7$, $R^8$, $R^9$ and $R^{10}$ are each methyl and
$R^{11}$ is hydrogen,
B is a direct bond, —CH$_2$— or —CH$_2$—CH$_2$— and
$R^5$ is hydrogen, cyano, hydroxyl or
M-B-$R^5$ is a group of the formulae
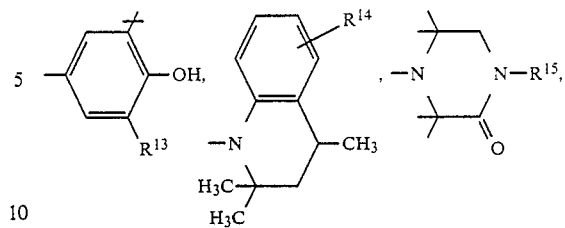
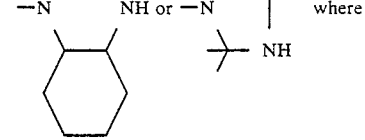
where
$R^{13}$ is methyl or tert-butyl,
$R^{14}$ is hydrogen, C$_1$–C$_4$-alkyl or C$_1$–C$_4$-alkoxy and
$R^{15}$ is C$_1$–C$_{12}$-alkyl.
* * * * *